United States Patent [19]

Lightner

[11] 4,418,648

[45] Dec. 6, 1983

[54] PROCESS FOR THE REDUCTION OF GILL DISEASE IN SHRIMP

[75] Inventor: Donald V. Lightner, Tucson, Ariz.

[73] Assignee: Marine Culture Enterprises, Atlanta, Ga.

[21] Appl. No.: 305,434

[22] Filed: Sep. 25, 1981

Related U.S. Application Data

[63] Continuation of Ser. No. 31,555, Apr. 19, 1979, abandoned.

[51] Int. Cl.$^3$ ............................................. A01K 61/00
[52] U.S. Cl. ........................................ 119/2; 424/294
[58] Field of Search ............................ 119/2; 424/294

[56] References Cited

U.S. PATENT DOCUMENTS 3,473,509  3/1967  Miyamura ............................... 119/2
3,998,186  12/1976  Hodges .................................... 119/2

OTHER PUBLICATIONS

Lightner, et al., Some Forms of Gill Disease in Penaeid Shrimp, 1975 pp. 347–364.
Lightner et al., A Possible Chemical Control Method for Filamentous Gill Disease; 1-25-76 pp. 473–481.
Sinderman, C. J.; Disease Diagnosis and Control in North American Marine Aquaculture 1977 pp. 31–35.
Lightner, D. V., Gill Disease; A Disease of Wild Cultured Penaeid Shrimp, 1978 Reprint No. 48.

Primary Examiner—Hugh R. Chamblee
Attorney, Agent, or Firm—Cahill, Sutton & Thomas

[57] ABSTRACT

Gill disease in shrimp may be beneficially reduced by a compound treatment of shrimp in their aquatic environment with a combination of permanganate ion and a triethanolaminecopper(II) complex marketed under the trademark Cutrine-Plus.

7 Claims, No Drawings

PROCESS FOR THE REDUCTION OF GILL DISEASE IN SHRIMP

This is a continuation of application Ser. No. 31,555, filed Apr. 19, 1979, now abandoned.

BACKGROUND OF THE INVENTION

Aquaculture, i.e. the specific cultivation of aquatic animals in a closed environment, has received serious and widespread investigation within the past twenty years as a result of an increasing awareness of the world food shortage. During this period several groups have investigated the potential of various types of aquaculture in conjunction with various species of aquatic animals. Several types of aquaculture have been studied including "Open Environment Aquaculture", wherein the aquatic animals are enclosed in large cages in their natural habitat, and "Pond Culture", wherein large ponds are stocked with aquatic animals. In conjunction with these studies several aquatic species have been studied including finfish, most notably catfish and trout, and shellfish, most notably oysters, each of which species has been raised with some degree of success. More recently, however, investigators have come to recognize the significant potential offered by the aquaculture of crustaceans, specifically shrimp, in "Controlled Environment Aquaculture" (CEA), i.e. the intensive culture of dense animal populations in an artificial and highly controlled system.

One embodiment of a CEA system is described in U.S. Pat. No. 3,998,186 to Hodges, the disclosures of which are herein incorporated by reference. CEA systems such as the one described in the Hodges patent may include one or more elongated waterways, or raceways, which contain an appropriate aquatic environment in which shrimp may be cultured. In addition, such a system may be equipped with an aquatic medium exchange means whereby new aquatic medium may be exchanged for used medium present in the raceway. Furthermore, the CEA system may include either a feed introduction means or a source of natural feed, or both, and an aeration device for maintaining a desired level of dissolved oxygen in the medium. Finally, a CEA system may include a clear, or partially opaque, canopy which covers the raceway and which may, if desired, allow sunlight to enter the aquatic medium.

The saltwater penaeid shrimp has been demonstrated to be culturable in captivity and to reach optimum market sizes in a few months. Hatchery techniques and reproductivity in captivity have been demonstrated for penaeid shrimp both in the United States and abroad. Furthermore, since the natural habitat of penaeid shrimp is salt water, the potential appears to exist for aquaculture of this species either in seawater or in brackish water from drilling sites. Penaeid shrimp, thus, appear to offer significant potential as a crop for Controlled Environment Aquaculture.

Freshwater shrimp appear to offer less promise as potential CEA species due to their lower fecundity, their aggressive behavior, and their intolerance to crowding. However, they do offer promise in less intensive aquaculture systems such as Pond Culture.

Before the Controlled Environment Aquaculture, or, indeed, any type of aquaculture, of shrimp can be considered to be commercially practical, however, most, if not all, of the procedures necessary for their culturing must be optimized in order that the venture will be economically viable. Thus an economical method for feeding the shrimp and an economical method for providing the optimum growth and survival rates within an aquatic environment must be developed. In this regard, one of the most important aspects of the aquaculture of shrimp is the treatment and prevention of diseases.

In high density populations, such as those utilized in CEA, diseases may be carried into the system by new aquatic medium which is circulated through the system by the aquatic medium exchange means and by wild females which are introduced into the system as spawners. In addition, certain disease-like conditions may result from nutritional deficiencies or abnormalities. Since the high population densities present in such systems make the animals more susceptible to stress (and thus to disease organisms present in aquatic medium), it is of the utmost importance to develop techniques for early diagnosis of such diseases and the most effective therapeutic agents for their treatment.

Several diseases and disease-like conditions have been found to afflict both wild and artificially cultured shrimp, with the severity of certain of these individual conditions being greater in artificial cultures due to the much higher population densities encountered in such systems. (see *Disease Diagnosis and Control in North American Marine Aquaculture*, Sinderman, C. J. Ed., Elsevier Scientific Publ. Co., New York, 1977, pp. 8–95.) Among the various diseases and disease-like conditions which afflict shrimp, gill disease presents an especially serious threat to their survival. (See Lightner, D. V., "Gill Disease: A Disease of Wild and Cultured Penaeid Shrimp", presented at the 66th International Council for the Exploration of the Sea, Copenhagen, Denmark, 1978.) The term gill disease encompasses a complex of several diseases which are developed by penaeid shrimp, both in wild environments that receive industrial or marine sewage, such as near-shore or estaurine waters, and in aquacultural systems that necessarily contain high levels of feed and/or natural waste due to the high population densities present. The majority of the organisms involved in gill disease of penaeid shrimp are free living organisms and are, thus, not true pathogens, but infestations. Nevertheless, when attached to, and abundant on, the gills, these organisms cause mortality indirectly by interfering with respiration either by preventing sufficient water-flow over the gills or by reducing gas exchange across gill surfaces.

Among the several organisms which are included under the general term of gill disease is a filamentous micro-organism which bears a close resemblance to *Leucothrix mucor*. This filamentous micro-organism has been identified on wild *P. aztecus* taken from estaurine waters near Galveston, Texas and on the gills and appendages of cultured *P. stylirostris, P. californiensis, P. vannamei*, and *P. mondon*. In every case the *L. mucor*-like micro-organism appears as unbranched thin tapering filaments of 3 to 5 μm diameter at the base, and tapering to 1-3 μm diameter apically. Filaments are attached to the shrimp's cuticle by an inconspicuous holdfast and extend to a length of from a few micrometers up to a millimeter or more. The filaments are sheathed by a thin inconspicuous sheath, and consist of many cells which are shorter in their axial measurement than they are in diameter. Gonidia are developed apically on the filaments. In gonidia formation, the apical region of a filament develops a beaded appearance caused by constriction of the outer cell wall at the transverse septa. Gonidia appear to be released by abcission from the filament either as single cells or as short chains, and to act as the transfer, or infective, stage of the micro-organism which ultimately locates and attaches to a new substrate.

This micro-organism, from penaeid shrimp does not appear to have been isolated and grown in pure culture, and, thus, its classification as *L. mucor* must be considered to be tentative. However, the *L. mucor*-like filaments found on penaeid shrimp appear to be morphologically indistinguishable from *L. mucor* as described by Harold and Stanier [*Biological Reviews* 19: 49–58 (1955)], Snellen and Raj [J. Bateriology, 101: 240–249 (1970)], and Skelton, et al. [J. Mar. Biol. Assoc. U.K., 55: 795–800 (1975)]. Because of its similarity to *Leucothrix mucor*, the filamentous micro-organism described above will be referred to as *L. mucor*. Nevertheless it is the micro-organism as described, rather than as tentatively identified as *L. mucor*, which has been found to be one of the major organisms in what is termed herein as gill disease.

Another filamentous organism is often present with *L. mucor* on the gills and appendages of penaeid shrimp. This organism is smaller in diameter (0.5 to 1.0 μm) and typically shorter than *L. mucor*, and is composed of individual cells that are longer than they are wide. This organism has been isolated from the gills and grown in pure culture. From such observations, this organism has been tentatively identified as Cytophaga sp. However, as was the case with *L. mucor*, the exact taxonomic position of this organism has not been conclusively proven. Thus, although this organism will be referred to herein as Cytophaga sp. herein, it is the organism as described, rather than as tentatively identified, which has been found in close association with *L. mucor* in penaeid shrimp.

Other filamentous organisms have been observed on the gills, appendages and general body surface of cultured penaeids, albeit with less frequency than *L. mucor* or Cytophaga sp. Certain filamentous blue-green algae including Lyngbya sp., Oscillatoria sp., and *Spirulina subsalsa* have been occassionally observed in sufficient amounts on the gills of cultured shrimp to have caused mortality, presumably due to respiratory failure. These organisms, with the exception of Spirulina, closely resemble *L. mucor* in morphology but can be readily distinguished by their larger diameter (greater than 4 μm) and the presence of chlorophyl pigments which give them a definite green to blue-green color.

Maintenance of good water quality and low population densities will minimize the presence of these filamentous forms of gill disease in penaeids. However, in high density aquaculture, such as CEA, chemotherapeutic treatments are often necessary to prevent shrimp mortalities resulting from these filamentous organisms. At present, the treatment of choice is a water soluble algaecide containing triethanolaminecopper(II) chelate manufactured under the trademark Cutrine-Plus by Applied Biochemists of Mequon, Wis. Cutrine-Plus has been used at 0.1–1.0 ppm copper(II) ion in 24 hr "flow through" treatments, (i.e. where aquatic media exchange is continued and the agent is constantly metered into the exchanging media) or at 0.25–0.5 ppm copper(II) ion in 4 to 6 hour "static" treatments (i.e. where aquatic media exchange is discontinued and the agent is added to the static environment and maintained in contact with the shrimp for the specified time after which aquatic media exchange is resumed). Permanganate ion (as potassium permanganate) at 5 to 10 ppm in 1 hr static treatments given every five to ten days has also been found to be effective to reduce these filamentous organisms. Thus, both Cutrine-Plus and permanganate ion are effective in treating gill disease, but, when used at the higher end of the stated dosage range, each treatment may cause shrimp mortality due to gill damage or agent toxicity.

The term gill disease also includes disease conditions caused by colonial peritrich protozoans, primarily Zoothamnium sp. and less commonly Epistylis sp. and Vorticella sp. These organisms have been reported to cause mortalities in cultured shrimp, are common in the epifauna of marine and brackish water environments, and are occassionally found on wild penaeids in nutrient rich estaurine waters.

Shrimp with heavy infestations of Zoothamnium sp., have a fuzzy-appearing mat on the surface of the gills, appendages, and occassionally on the carapace. Microscopic examination of wet mounts made from scrapings of these areas show Zoothamnium sp., to be branched colonial organism. Zoothamnium sp. have been observed on all four species of cultured penaeid shrimp discussed above.

Although less common among cultured shrimp, the protozoans Epistylis sp. and Vorticella sp. are occassionally observed on shrimp with gill disease. These organisms are similar in appearance to Zoothamnium sp., but Zoothamnium sp. may be distinguished from Epistylis sp. and Vorticella sp. because the former organism possesses a continuous myoneme that connects the stalks of each trophont within the colony so that the colony may contract as a unit. Epistylus lacks a contractile stalk, and, while Vorticella sp. is often colonial and possesses a contractile stalk, it does not have a continuous myoneme connecting individual members of the colony. Hence, the Vorticella sp. colonies do not contract as a unit as does Zoothamnium.

Like *L. mucor*, these peritrich protozoans cause disease and death in penaeid shrimp when they are abundant on the gills, although they cause no discernable histopathology and evoke no inflammatory response. As with the filamentous forms of gill disease, shrimp mortality due to protozoans, is presumed to result from hypoxia due to reduced respiratory efficiency of the gills.

Numerous other gill disease organisms are seen occassionally in association with *L. mucor* filaments on the gills of shrimp. Included among these organisms are various blue-green algae, eg. Enteromorpha sp. and Ulva sp., several diatom species, and numerous species of Gram negative bacteria, most commonly Vibrio sp. Various saprophytic fungi such as the imperfect fungus *Fusarium solani*, (which is responsible for a disease called black gill disease when it infects gill tissues) may also be present.

In order to ensure the economic viability of an aquaculture system such as the CEA of shrimp, both the individual weight gain of each animal and the survival rate during the grow-out period must be maximized in order to produce the maximum gross weight of shrimp. Since disease in general, and gill disease in particular, would be expected to exert a negative influence on both survival rate and individual weight gain, it is of the utmost importance to develop the most effective gill disease treatment process in order to reduce or eliminate this negative influence. In addition, since it appears that the filamentous gill disease organisms *L. mucor* and Cytophaga sp. appear to significantly enhance the ability of other gill disease forms, especially the algae and the protozoans, to flourish, it is of great importance to develop the most effective chemotherapeutic treatment for reduction of these filamentous organisms.

Thus, while the individual use of either Cutrine-Plus or potassium permanganate is well known to be effective in the treatment of L. mucor and Cytophaga sp. in shrimp, the development of a treatment which shows increased effectiveness is of great importance to the Controlled Environment Aquaculture of shrimp.

SUMMARY

It has now been discovered that shrimp having gill disease may be beneficially reduced by a compound treatment with permanganate ion and Cutrine-Plus. According to the preferred embodiment of the process, the aquatic environment containing the shrimp is isolated to provide a static environment, a permanganate ion source is added to pretreat the environment, Cutrine-Plus is added to the pretreated aquatic environment, the shrimp are maintained in contact with the treated aquatic environment for an effective treatment time, and the treated aquatic environment is flushed with untreated media to remove the permanganate ion, the Cutrine-Plus, and their reaction products at the expiration of the treatment time.

DESCRIPTION OF THE PREFERRED EMBODIMENT

A complete understanding of the invention will be gained by those skilled in the art from the following description.

As discussed above, the individual factors of survival rate and average weight gain, as well as the overall gross weight gain, or increase in biomass, of a CEA system must be maximized by a gill disease treatment process before that system will reach its maximum production. As also discussed above, the determination of the optimum chemotherapeutic gill disease treatment will involve the determination of the doseage at which the treatment both minimizes loss due to gill disease and, at the same time, minimizes loss due to toxicity of the treatment itself.

In order to test the comparative efficacy of permanganate ion and Cutrine-Plus, both singly and in combination, in the treatment of gill disease in shrimp, parallel experiments were performed on juvenile shrimp for an extended period according to the protocol set forth in Experiment I.

EXPERIMENT I

Batches of 1000 juvenile (approximately 5 mos. old and 5 to 7.5 g in wt.) blue shrimp (Penaeus stylirostris) were weighed for initial biomass and placed in each of 8 separate controlled environment tanks which contained approximately 1800 liters of seawater and which had bottom areas of 5 $M^2$. Each batch of shrimp was maintained in the controlled environment tank with regular feedings of approximately 1 g of feed per 20 g of biomass daily. The treatment was continued along with seawater exchange and seawater aeration over a 12 week test period. One tank was maintained untreated as a control against which the efficacy of each treatment could be measured. Chemotherapeutic treatments were administered every seventh day under static conditions by discontinuing the seawater exchange. In order to prevent the ingestion of feed during the treatments, feeding was discontinued prior to discontinuing seawater exchange and not resumed until after completion of the treatment. Treatment periods for individual permanganate ion or Cutrine-Plus chemotherapeutic treatments were of a six hour duration, whereas compound treatments using a combination of $KMnO_4$ and Cutrine-Plus were administered by adding the permanganate ion (as $KMnO_4$ dissolved in approximately 1 gallon of water), allowing the permanganate ion to pretreat the seawater for approximately 15 minutes, subsequently introducing the Cutrine-Plus at the end of the 15 minute pretreatment period, and maintaining the shrimp in contact with permanganate ion and Cutrine-Plus for an additional five hours, forty-five minutes. Each tank was monitored for shrimp mortality, and dead shrimp were removed as observed. One day prior to each of the weekly treatments, five live shrimp were chosen at random from each tank, and their gills were biopsied, examined microscopically, and rated for filamentous forms of gill disease. At the end of the 12 week experiment, the shrimp from each tank were counted to determine mortality rate and weighed in gross to determine average individual, and gross, weight gain. The results of Experiment I are tabulated in Table I.

TABLE I

| Batch No. | Treatment | Initial Count | Initial Biomass (g) | Initial Avg. Wt. (g) | Final Count | Final Biomass (g) | Final Avg. Wt. (g) | Mortality | % Avg. Wt. Gain of Survivors | % Gain in Biomass |
|---|---|---|---|---|---|---|---|---|---|---|
| 1 | CONTROL | 1000 | 7570 | 7.57 | 280 | 5639 | 20.2 | 72% | 167% | −25 |
| 2 | 2.5 p.p.m. $KMnO_4$ | 1000 | 7570 | 7.57 | 537 | 11105 | 20.7 | 46% | 173% | 47 |
| 3 | 5.0 p.p.m. $KMnO_4$ | 1000 | 5040 | 5.04 | 494 | 7509 | 15.2 | 50% | 201% | 49 |
| 4 | 0.50 p.p.m. Cu(II) as Cutrine-Plus | 1000 | 7570 | 7.57 | 585 | 12706 | 21.7 | 42% | 186% | 68 |
| 5 | 5.0 p.p.m. $KMnO_4$ + 0.5 p.p.m. Cu(II) as Cutrine-Plus | 1000 | 7570 | 7.57 | 642 | 9733 | 15.2 | 36% | 100% | 29 |
| 6 | 5.0 p.p.m. $KMnO_4$ + 0.25 p.p.m. Cu(II) as Cutrine-Plus | 1000 | 5040 | 5.04 | 716 | 9952 | 13.9 | 28% | 175% | 97 |
| 7 | 2.5 p.p.m. $KMnO_4$ + 0.25 p.p.m. Cu(II) as Cutrine-Plus | 1000 | 7570 | 7.57 | 771 | 15004 | 19.5 | 23% | 158% | 99 |
| 8 | 2.5 p.p.m. $KMnO_4$ + | 1000 | 7570 | 7.57 | 785 | 15558 | 19.8 | 22% | 161% | 106 |

TABLE I-continued

| Batch No. | Treatment | Initial Count | Initial Biomass (g) | Initial Avg. Wt. (g) | Final Count | Final Biomass (g) | Final Avg. Wt. (g) | Mortality | % Avg. Wt. Gain of Survivors | % Gain in Biomass |
|---|---|---|---|---|---|---|---|---|---|---|
| | 0.50 p.p.m. CU(II) as Cutrine-Plus | | | | | | | | | |

As noted above, the gills of live shrimp were biopsied and examined weekly for *L. mucor*. In all cases, shrimp from the control group (Batch 1) exhibited a greater degree of *L. mucor* than did those which were chemically treated. Comparison of *L. mucor* levels for shrimp selected from Batches 2–8 showed no statistically significant differences in *L. mucor* levels. This lack of statistically significant differences between shrimp given single agent treatment and those given compound treatment reflects, at least in part, the inherent bias of the sampling method, i.e., selecting only live shrimp, rather than both live and dead shrimp, for inspection. In this regard, if it is assumed that the shrimp which failed to survive would have exhibited lethal (high) levels of *L. mucor*, then differences in *L. mucor* presence in the various batches would be expected to be reflected in the respective figures for percent mortality.

The data shown in Table I presents an informative view of shrimp aquaculture and of the reaction of aquaculturally raised shrimp to the various chemotherapeutic treatment processes employed. Batch 1 (untreated) incurred disastrous mortality losses (72%) but those shrimp which survived almost tripled in weight. A comparison of the figures from Batch 1 with those of Batches 2 and 4 (single agent treatment processes) shows that both the rate of survival and the average weight of the survivors were increased by chemotherapeutic treatment with low levels of either agent administered singly. Finally, comparing these results for single agent treatment with those for Batches 6, 7 and 8 indicates a significant improvement in percent survival for such compound treatments over that for single agent treatment. The percent average weight gain for the survivors from Batches 6, 7 and 8 is approximately equal to that for Batch 1, but is somewhat lower (approximately 20%) than those for Batches 2 and 4, perhaps due to the fact that the population densities in the latter batches are approaching the carrying capacity of the tanks. Batches 3 and 5 show a higher mortality rate than the other batches in their groups (2–4 and 5–8 respectively), and Batch 5 shows the lowest average weight gain. Why such should be the case is not completely understood, but may indicate the onset of agent toxicity effects resulting from the high dosage levels of chemotherapeutic agents in their respective batches. With the exception of Batch 5, however, the combined effect of survival rate and average weight gain, as expressed by the percent gain in Biomass, clearly indicates the superiority of the compound treatment process over the single agent treatment process for gill disease.

Experiment I tested the effects of various gill disease treatment processes on shrimp during a selected period in their growth, i.e., from about 5–7 g to about 20 g, where the effect of gill disease on both mortality and on average weight gain is expected to have significant impact on the economic viability of shrimp aquaculture. Gill disease does, however, afflict shrimp of larger size, i.e., greater than 20 g, where percent average weight gain is small, as well as of smaller size, i.e., less than 4 g, where percent average weight gain is large. In order to test the effectiveness of both single agent treatment and compound treatment of these growth stages, additional experiments were run on larger shrimp (Experiment II) and on smaller shrimp (Experiment III) as described below.

EXPERIMENT II

The protocol of Experiment II was essentially similar to that of Experiment I except that five hundred (500) twenty gram (20 g) blue shrimp were used and the treatment period was for six weeks. A first batch was left untreated as a control, a second batch was treated weekly with 0.25 p.p.m. copper (II) ion (as Cutrine-Plus), and a third group was given a compound treatment of 2.5 p.p.m. KMnO$_4$ for a 15 minute pretreatment period followed by addition of 0.25 p.p.m. copper (II) ion (as Cutrine-Plus). The results of Experiment II are shown in Table II.

TABLE II

| Batch No. | Treatment | Initial Count | Initial Biomass (g) | Initial Avg. Wt. (g) | Final Count | Final Biomass (g) | Final Avg. Wt. (g) | Mortality | % Avg. Wt. Gain of Survivors | % Gain in Biomass |
|---|---|---|---|---|---|---|---|---|---|---|
| 1 | CONTROL | 500 | 10,000 | 20.0 | 171 | 4300 | 25.2 | 65.8% | 26.0% | −57 |
| 2 | 0.25 p.p.m. Cu(II) as Cutrine-Plus | 500 | 10,000 | 20.0 | 425 | 11450 | 26.9 | 15.0% | 34.5% | 14 |
| 3 | 2.5 p.p.m. KMnO$_4$ + 0.25 p.p.m. Cu(II) as Cutrine-Plus | 500 | 10,000 | 20.0 | 474 | 11400 | 24.0 | 5.2% | 20.0 | 14 |

The results shown in Table II demonstrate drastic mortality losses (near 70%) for the control (Batch 1). Such losses are reduced to 15% by the single agent treatment with Cutrine-Plus. With the compound treatment, however, the mortality losses are reduced by two-thirds to approximately 5%. Weight gain percentages for all three Batches were predictably lower than those found in Experiment I due both to the shorter duration of the experiment (6 weeks vs. 12 weeks) and to the fact that the test animals were nearly adult size (20 g) and thus had lower growth rates than did the smaller shrimp (5–7 g) of Experiment I. As in Experiment I, the average weight gain in shrimp surviving the single agent treatment (Batch 2) was higher than that of the control, whereas, that of shrimp surviving the compound treatment (Batch 3) was slightly lower than that of the control.

The results of Experiment II as reflected in the individual mortality rates demonstrate the superiority of the compound treatment process over the single agent treatment process for gill disease for mature shrimp.

EXPERIMENT III

In order to test the effectiveness of gill disease treatments on small shrimp, 900 five month old *Penaeus californiensis* having an average weight of 3.1 grams, were placed in each of three tanks. The first batch was left untreated as a control, the second batch was treated weekly with 0.25 p.p.m copper (II) (as Cutrine-Plus), and the third batch was subjected to a compound treatment of 2.5 p.p.m. permanganate ion (as $KMnO_4$) plus 0.25 p.p.m. copper (II) (as Cutrine-Plus) using the protocol described in Experiment II. The treatments were administered every seventh day for was six weeks. The results of Experiment III are as shown in Table III.

in shrimp mortality from the agent itself. Experiment I shows an average survival for shrimp treated with a single agent of 54% while those given the compound treatment showed an average survival of 73%. Similar, although less striking, increases in percent survival are shown in Experiments II and III where the treatment period was reduced from twelve to six weeks in order to limit the test duration to encompass specific growth stages for both larger (Experiment II) and smaller (Experiment III) shrimp.

While not wishing to be bound by any particular theory of how the compound treatment functions, it appears that the pretreatment of the aquatic environment with permanganate ion functions to reduce the biochemical oxygen demand (BOD) and the chemical oxygen demand (COD) of the aquatic media by reducing dissolved and suspended organic material and to, thereby, boost the level of dissolved oxygen in the

TABLE III

| Batch No. | Treatment | Initial Count | Initial Biomass (g) | Initial Avg. Wt. (g) | Final Count | Final Biomass (g) | Final Avg. Wt. (g) | Mortality | % Avg. Wt. Gain of Survivors | % Gain in Biomass |
|---|---|---|---|---|---|---|---|---|---|---|
| 1 | CONTROL | 900 | 2790 | 3.10 | 218 | 2210 | 10.1 | 75% | 225% | −21 |
| 2 | 0.25 p.p.m. Cu(II) as Cutrine-Plus | 900 | 2790 | 3.10 | 804 | 8088 | 10.0 | 9% | 222% | 190 |
| 3 | 2.5 p.p.m. $KMnO_4$ + 0.25 p.p.m. Cu(II) as Cutrine-Plus | 900 | 2790 | 3.10 | 823 | 8658 | 10.5 | 7% | 239% | 208 |

As in both Experiment I and II, the results of Experiment III for small (3 g) shrimp show catastrophic mortalities (75%) due to gill disease in the control group, with both single agent and compound treatment processes dramatically reducing these mortalities. In Experiment III, the compound treatment proved to be significantly superior to the single agent treatment both in reducing the percent mortality and in increasing the average weight of the surviving shrimp. As a result of its superiority in both categories, the gross weight (Biomass) increase for the compound treatment significantly exceeded that found for the single agent treatment for these small shrimp.

Three facts are amply demonstrated by the results of Experiments I, II, and III. The first fact is that when artificially cultured shrimp are not treated for gill disease catastrophic losses on the order of 65-75% occur. That a crop loss of such magnitude could destroy the economic viability of an aquaculture system is unquestionable.

The second fact is that the treatment of artificially cultured shrimp with either permanganate ion or with the chelated copper algaecide Cutrine-Plus substantially increases the survival rate of the shrimp. Both of these facts are known to those skilled in the art, and thus were it not for the equally well known fact that each of these chemotherapeutic agents may cause shrimp mortality themselves when administered above certain levels, the dosage of either agent could be simply increased to realize an increased survival rate among the diseased shrimp.

The third fact shown by the Experimental results, and the one which demonstrates the utility of the present invention, is that the two agents may be combined in a compound treatment for gill disease in shrimp to realize significant increases in the survival rate of such shrimp over and above that realized with the use of either agent singly and without a concomittant increase aquatic environment to allow greater respiratory efficiency. Cutrine-Plus, on the other hand, would appear to attack the filamentous micro-organism itself. The compound treatment is believed to be effective over a broad range of permanganate ion concentration of from about 1 to about 10 p.p.m. when used in combination with a broad range of copper (II) ion concentrations (as Cutrine-Plus) of from about 0.1 p.p.m. to about 5.0 p.p.m. Within this broad range and in order to minimize losses due to agent toxicity, it is preferred to utilize permanganate ion within a range of from about 2.5 p.p.m. to 5.0 p.p.m. in conjunction with Cu(II) ion concentrations (as Cutrine-Plus) of from about 0.1 to about 0.1. Finally, the optimum concentrations for use in the compound treatment of gill disease in penaeid shrimp are 2.5 p.p.m. permanganate ion and 0.25 to 0.5 p.p.m. copper(II) ion (as Cutrine-Plus).

In addition to the concentration of the two chemical agents discussed above, qualitative observation of the treatment appears to support the finding that the compound treatment is more effective and when the tank or raceway is cleaned by vacuuming or flushing prior to the treatment in order to reduce BOD, COD, and suspended or dissolved organic materials. Such a reduction would seem to increase the effectiveness of the permanganate ion pretreatment as it would seem to increase the levels of dissolved oxygen in the aquatic environment.

All of the experiments described hereinabove utilize a permangate ion pretreatment period of approximately 15 minutes which appears to be the optimum period for effectiveness. Nevertheless it is believed that such pretreatment period may vary over a broad range of from 0 to 60 minutes with 15 to 45 minutes being preferred.

Although static treatment periods of six hours were used at weekly intervals in the experiments recounted hereinabove, it is conceivable that shorter or longer treatments administered more or less frequently, respectively, could result in equally beneficial results, provided that the status of gill disease in the shrimp is monitored and treatments are administered as needed. As with many such disease treatment processes, the concentration of the chemotherapeutic agents, the frequency of administration and the duration of treatment are all factors which, within obvious limits, are dependant rather than independant. The experimental results reported above indicate an optimum treatment to be a six hour static treatment administered weekly with 2.5 p.p.m. permanganate ion and 0.25 to 0.5 p.p.m. copper (II) ion (as Cutrine-Plus). The present invention, however, should not be viewed as restricted to certain concentrations, treatment times and treatment frequencies but rather should be seen to be limited only to the discovery that the use of the two chemotherapeutic agents, i.e. permanganate ion and Cutrine-Plus, is a more beneficial treatment for gill disease than is either agent administered separately.

From the foregoing description it will be apparent that changes in the process, steps, or order of steps as described herein may occur to persons skilled in the art without departing from the scope and spirit of the invention. Accordingly, the forgoing description is considered to be only exemplary of the invention as defined in the appended claims.

What is claimed is:

1. A process for the reduction of gill disease in penaeid shrimp raised in a controlled environment, said controlled environment of the type wherein said penaeid shrimp are periodically supplied with feed and are confined to a seawater-containing raceway having a means for intermittent seawater replacement and an aeration device for oxygenation of said seawater said process comprising:
   a. dicontinuing the supplying of feed into said raceway;
   b. closing said means for seawater replacement to provide a static seawater environment;
   c. cleaning suspended or settled organic matter from said raceway;
   d. introducing potassium permanganate into said raceway in an amount sufficient to provide initial concentration of said potassium permanganate in said raceway of from about 2.0 p.p.m. to about 4.0 p.p.m.;
   e. allowing said potassium permanganate to pretreat said seawater for a pretreatment period of from about 15 minutes to about 45 minutes;
   f. subsequently introducing Cutrine-Plus into said pretreated seawater in an amount sufficient to provide an initial concentration of Cu(II) (as Cutrine-Plus) in said seawater of from about 0.25 to about 0.5 p.p.m.;
   g. maintaining said penaeid shrimp in contact with said seawater containing said potassium permanganate and said Cutrine-Plus for a treatment time of from about 5 to about 7 hours;
   h. opening said seawater replacement means to flush said raceway with seawater at the expiration of said treatment time to remove said potassium permanganate, said Cutrine-Plus and their reaction products from said raceway.

2. A process for reducing gill disease in shrimp in controlled environment aquaculture comprising introducing into the water constituting said environment a source of permanganate ion in sufficient quantity to yield a permanganate ion concentration in the water of from about 1 p.p.m. to about 10 p.p.m., and a sufficient amount of triethanolamine copper (II) to provide a CU (II) concentration in the water of from about 0.1 p.p.m. to about 5.0 p.p.m.

3. The process as set forth in claim 2 wherein the source of permanganate ion is potassium permanganate.

4. The process as set forth in claim 2 in which said permanganate ion concentration is from about 2.0 p.p.m. to about 4.0 p.p.m. and said Cu (II) concentration is from about 0.25 p.p.m. to about 0.5 p.p.m.

5. The process as set forth in claim 2 wherein said source of permanganate ion and said triethanolaminecopper (II) are introduced into said environment periodically for periods of from about 5 hours to about 7 hours.

6. The process as set forth in claim 2 further including removing suspended and settled organic matter from the environment prior to introducing said source of permanganate ion and said triethanolaminecopper (II).

7. The process as set forth in claim 2 wherein said source of permanganate ion is introduced prior to introduction of said triethanolaminecopper (II).

* * * * *